United States Patent
Tanaka et al.

(10) Patent No.: US 9,513,545 B2
(45) Date of Patent: Dec. 6, 2016

(54) HOMOADAMANTANE DERIVATIVES, PROCESS FOR PREPARING SAME, AND PHOTORESIST COMPOSITIONS

(75) Inventors: Shinji Tanaka, Ichihara (JP); Yoshitaka Uenoyama, Ichihara (JP); Hidetoshi Ono, Ichihara (JP); Naoya Kawano, Ichihara (JP); Katsuki Ito, Ichihara (JP)

(73) Assignee: Osaka Organic Chemical Industry Ltd., Osaka-shi (JP)

( * ) Notice: Subject to any disclaimer, the term of this patent is extended or adjusted under 35 U.S.C. 154(b) by 47 days.

(21) Appl. No.: 13/816,071

(22) PCT Filed: Jul. 26, 2011

(86) PCT No.: PCT/JP2011/004198
§ 371 (c)(1),
(2), (4) Date: Feb. 8, 2013

(87) PCT Pub. No.: WO2012/020546
PCT Pub. Date: Feb. 16, 2012

(65) Prior Publication Data
US 2013/0143157 A1   Jun. 6, 2013

(30) Foreign Application Priority Data

Aug. 12, 2010 (JP) ................. 2010-180908

(51) Int. Cl.
*C08F 220/28* (2006.01)
*C08F 220/30* (2006.01)
(Continued)

(52) U.S. Cl.
CPC ............ *G03F 7/004* (2013.01); *C07D 313/06* (2013.01); *C07D 313/10* (2013.01); *C08F 220/28* (2013.01); *G03F 7/0397* (2013.01); *C08F 220/30* (2013.01)

(58) Field of Classification Search
CPC . C07D 313/06; C07D 313/10; C08F 220/28; C08F 220/30
See application file for complete search history.

(56) References Cited

U.S. PATENT DOCUMENTS 6,303,266 B1   10/2001   Okino et al.
6,486,330 B1   11/2002   Nakano
(Continued)

FOREIGN PATENT DOCUMENTS

CN    101271273 A    9/2008
EP    1 081 150 A1   3/2001
(Continued)

OTHER PUBLICATIONS

English Translation of JP2003149812.*
(Continued)

*Primary Examiner* — Cynthia H Kelly
*Assistant Examiner* — Anna Malloy
(74) *Attorney, Agent, or Firm* — Oblon, McClelland, Maier & Neustadt, L.L.P.

(57) ABSTRACT

A compound represented by the following formula (I), wherein $R^1$ is a hydrogen atom, a halogen atom, a methyl group or a trifluoromethyl group.

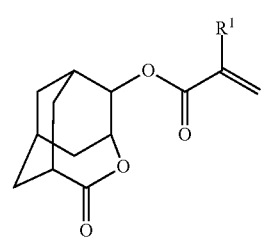

(I)

14 Claims, 1 Drawing Sheet

(51) Int. Cl.
*C07D 313/06* (2006.01)
*C07D 313/10* (2006.01)
*G03F 7/004* (2006.01)
*G03F 7/039* (2006.01)

(56) References Cited

U.S. PATENT DOCUMENTS

| | | | |
|---|---|---|---|
| 7,456,311 | B2 | 11/2008 | Hatakeyama et al. |
| 7,528,279 | B2 | 5/2009 | Hatakeyama et al. |
| 2002/0098441 | A1 | 7/2002 | Okino et al. |
| 2003/0149225 | A1 | 8/2003 | Okino et al. |
| 2004/0043324 | A1 | 3/2004 | Okino et al. |
| 2005/0031990 | A1 | 2/2005 | Okino et al. |
| 2005/0031991 | A1 | 2/2005 | Okino et al. |
| 2005/0037283 | A1 | 2/2005 | Okino et al. |
| 2005/0037284 | A1 | 2/2005 | Okino et al. |
| 2005/0048400 | A1 | 3/2005 | Okino et al. |
| 2006/0160017 | A1 | 7/2006 | Takemoto et al. |
| 2007/0111138 | A1 | 5/2007 | Rahman et al. |
| 2008/0076063 | A1 | 3/2008 | Yoshida et al. |
| 2008/0081925 | A1 | 4/2008 | Sakamoto et al. |
| 2008/0274426 | A1 | 11/2008 | Fuji et al. |
| 2008/0318156 | A1 | 12/2008 | Tanaka et al. |
| 2009/0156854 | A1 | 6/2009 | Hatakeyama et al. |
| 2009/0162784 | A1 | 6/2009 | Ogata et al. |
| 2009/0162788 | A1 | 6/2009 | Hada et al. |
| 2009/0269700 | A1 | 10/2009 | Yonemura et al. |
| 2010/0266954 | A1 | 10/2010 | Ito et al. |
| 2012/0129104 | A1* | 5/2012 | Aqad et al. ............... 430/285.1 |
| 2012/0164580 | A1 | 6/2012 | Hada et al. |
| 2013/0022914 | A1 | 1/2013 | Tanaka et al. |

FOREIGN PATENT DOCUMENTS

| | | | |
|---|---|---|---|
| JP | 4-39665 | A | 2/1992 |
| JP | 2000-122294 | A | 4/2000 |
| JP | 2001-72674 | A | 3/2001 |
| JP | 2001-240625 | A | 9/2001 |
| JP | 2003149812 | A * | 5/2003 |
| JP | 2006-201762 | A | 8/2006 |
| JP | 2008-69146 | A | 3/2008 |
| JP | 2008-268916 | A | 11/2008 |
| JP | 2009-515944 | A | 4/2009 |
| JP | 2009-98448 | A | 5/2009 |
| JP | 2009-149588 | A | 7/2009 |
| JP | 2009-527019 | A | 7/2009 |
| JP | 2009-223024 | A | 10/2009 |
| JP | 2009-282494 | A | 12/2009 |
| WO | WO 2006/038477 | A1 | 4/2006 |

OTHER PUBLICATIONS

Combined Chinese Office Action and Search Report issued Dec. 26, 2013 in Patent Application No. 201180039140.4 (with English translation of categories of cited documents).
Office Action issued Sep. 4, 2014 in Chinese Patent Application No. 201180039140.4.
International Search Report issued Sep. 13, 2011 in PCT/JP2011/004198.
International Preliminary Report on Patentability and Written Opinion issued Mar. 21, 2013 in PCT/JP2011/004198 Filed Jul. 26, 2011 submitting English translation only.
Helmut Duddeck, et al., "Rearrangements of Oxahomoadamantane Derivatives in Acidic Media", Journal of Organic Chemistry, vol. 46, No. 26, 1981, pp. 5332-5336.
Decision of Rejection issued May 20, 2015, in Chinese Patent Application No. 201180039140.4.
Chinese Office Action issued Mar. 30, 2016 in Patent Application No. 201180039140.4.

* cited by examiner

| ROTATION ANGLE [°] | DIPOLE MOMENT [Debye] | |
|---|---|---|
| | COMPOUND A | COMPOUND B |
| 0 | 6.384 | 6.367 |
| 20 | 6.986 | 6.939 |
| 40 | 7.423 | 7.279 |
| 60 | 7.577 | 7.316 |
| 80 | 7.699 | 7.348 |
| 100 | 7.726 | 7.322 |
| 120 | 7.007 | 7.024 |
| 140 | 6.319 | 6.294 |
| 160 | 5.668 | 5.406 |
| 180 | 5.403 | 5.318 |
| 200 | 5.011 | 5.145 |
| 220 | 3.937 | 4.204 |
| 240 | 3.523 | 3.679 |
| 260 | 3.81 | 3.897 |
| 280 | 4.302 | 4.564 |
| 300 | 5.202 | 4.656 |
| 320 | 5.783 | 4.715 |
| 340 | 5.997 | 5.554 |
| 360 | 6.384 | 6.367 |
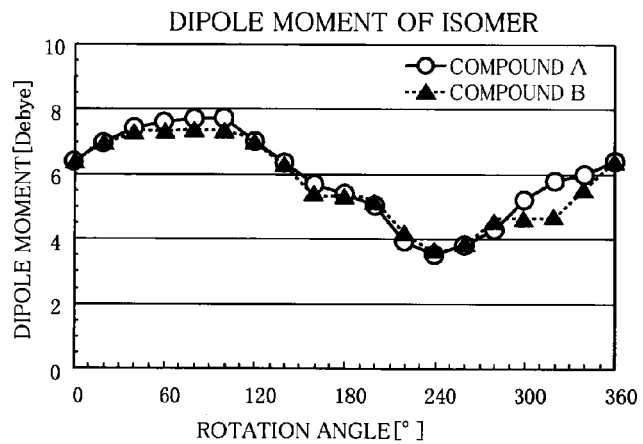

HOMOADAMANTANE DERIVATIVES, PROCESS FOR PREPARING SAME, AND PHOTORESIST COMPOSITIONS

TECHNICAL FIELD

The invention relates to a novel homoadamantane derivative, a method for producing the same, a (meth)acrylic polymer, a positive photoresist composition, and a method for forming a resist pattern.

BACKGROUND ART

In recent years, a photolithographic process used to produce semiconductor devices has been desired to form a finer pattern along with miniaturization of semiconductor devices. Various methods for forming a fine pattern using a photoresist material that responds to short-wavelength light such as KrF excimer laser light, ArF excimer laser light, or $F_2$ excimer laser light have been studied, and a novel photoresist material that responds to short-wavelength light such as excimer laser light has been desired.

Various phenol resin-based photoresist materials have been developed. However, since these materials absorb light to a large extent due to the aromatic ring, it is difficult to obtain pattern accuracy that can deal with miniaturization In order to deal with the above problem, a polymer obtained by copolymerizing polymerizable compounds having an alicyclic skeleton (e.g., 2-methyl-2-adamantyl methacrylate) has been proposed as a photoresist used for a semiconductor production process that utilizes ArF excimer laser light (see Patent Document 1, for example).

A line width of 32 nm or less is being implemented through the development of microfabrication technology. However, it is difficult to meet various requirements (e.g., adhesion to substrate, exposure sensitivity, resolution, pattern shape, exposure depth, and surface roughness) using only the existing technology. Specifically, the surface of the resulting pattern may show roughness (LER or LWR) or poor flatness when using the existing technology. When using liquid immersion lithography that has been developed in recent years, defects or the like may occur in the resist pattern due to the immersion medium. Moreover, development of a photoresist that exhibits higher sensitivity has been desired for a semiconductor production process that utilizes extreme ultraviolet (EUV) light (wavelength: 13.5 nm) in order to improve the throughput.

A polymer obtained by copolymerizing polymerizable compounds having a cyclic lactone structure has been used as a photoresist used for a semiconductor production process that utilizes ArF excimer laser light in order to improve adhesion to a substrate. 1-(5-Oxo-4-oxa-5-homoadamantyl) methacrylate has been proposed as a lactone having a homoadamantane skeleton, and a photosensitive composition and a pattern-forming method that can form a resist pattern that exhibits high transparency to short-wavelength light and high dry etching resistance, can be developed using an alkali, and exhibits excellent adhesion and resolution have been proposed (see Patent Document 2, for example). However, since a polymerizable compound having a cyclic lactone structure such as the above homoadamantyl methacrylate compound does not have acid-labile properties, such a polymerizable compound does not function as a positive photoresist when used alone. Therefore, it is necessary to copolymerize such a polymerizable compound with an acid-labile monomer such as tert-butyl methacrylate or 2-methyl-2-adamantyl methacrylate.

A photoacid generator (PAG) is indispensable for a positive photoresist in order to implement photosensitivity (dissociation due to acid). Attempts have been made to provide a PAG with acid-labile properties in order to suppress or reduce roughness (LER or LWR) of the surface of the pattern that may occur due to miniaturization (see Patent Documents 3 to 6, for example). However, it is necessary to increase the mutual solubility of a PAG with a photoresist resin, or more uniformly disperse a PAG in a photoresist resin in order to further reduce roughness.

In recent years, an acid-labile unit having an adamantane skeleton or a cyclic lactone structure has been extensively introduced in the development of a low-molecular-weight (monomolecular) positive photoresist that aims at reducing roughness (see Patent Documents 7 to 10, for example). However, satisfactory results have not been obtained by such a method.

RELATED-ART DOCUMENT

Patent Document

Patent Document 1: JP-A-4-39665
Patent Document 2: JP-A-2000-12294
Patent Document 3: JP-A-2009-149588
Patent Document 4: JP-A-2009-282494
Patent Document 5: JP-A-2008-69146
Patent Document 6: JP-T-2009-515944
Patent Document 7: JP-T-2009-527019
Patent Document 8: JP-A-2009-98448
Patent Document 9: JP-A-2009-223024
Patent Document 10: JP-A-2006-201762

SUMMARY OF THE INVENTION

An object of the invention is to provide a polymer that can suppress or reduce roughness and defects, and exhibits excellent solubility, mutual solubility, exposure sensitivity, and the like when used for a positive photoresist, and a monomer that produces the polymer.

According to the invention, the following compounds or the like are provided.

1. A compound represented by the following formula (I):

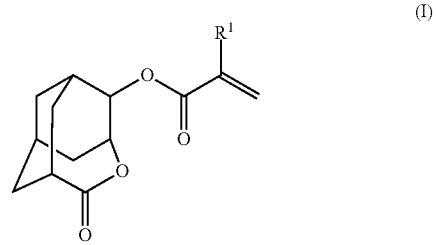

wherein $R^1$ is a hydrogen atom, a halogen atom, a methyl group or a trifluoromethyl group.

2. A method for producing the compound according to claim 1, comprising reacting 5-oxo-4-oxa-5-homoadamantan-2-ol represented by the following formula (A) with a (meth)acrylic acid compound or its derivative.

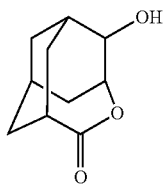

(A)

3. The production method according to 1, wherein the 5-oxo-4-oxa-5-homoadamantan-2-ol is reacted with methacrylic anhydride.
4. A (meth)acrylic polymer obtained by polymerizing the compound according to 1.
5. A positive photoresist composition comprising the (meth) acrylic polymer according to 4 and a photoacid generator.
6. A method for forming a resist pattern comprising the steps of:
forming a photoresist film on a substrate by using the positive photoresist composition according to 5;
selectively exposing the photoresist film to light; and
subjecting the photoresist film which has been selectively exposed to an alkaline development treatment to form a resist pattern.

The invention thus provides a polymer that can suppress or reduce roughness and defects, and exhibits excellent solubility, mutual solubility, exposure sensitivity, and the like when used for a positive photoresist, and a monomer that produces the polymer.

BRIEF DESCRIPTION OF DRAWINGS

FIG. 1 is a view illustrating the dipole moment measurement results for the compounds obtained in Example 1 and Comparative Example 1.

DESCRIPTION OF EMBODIMENTS

A compound according to the invention is represented by the following formula (I).

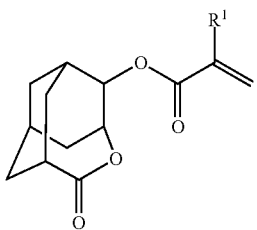

(I)

wherein $R^1$ is a hydrogen atom, a halogen atom, a methyl group, or a trifluoromethyl group.

$R^1$ is preferably a hydrogen atom or a methyl group.

The homoadamantane derivative according to the invention that is represented by the formula (I) may be produced by reacting 5-oxo-4-oxa-5-homoadamantan-2-ol represented by the following formula (A) with a (meth)acrylic acid compound or its derivative in the presence of a basic catalyst, for example. The above production method can produce a highly pure homoadamantane derivative in high yield. Note that the homoadamantane derivative may also be produced by reacting 5-oxo-4-oxa-5-homoadamantan-2-ol with a (meth)acrylic acid compound or its derivative in the absence of a catalyst.

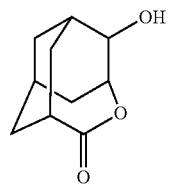

(A)

Examples of the (meth)acrylic acid compound include acrylic acid, methacrylic acid, 2-fluoroacrylic acid, 2-trifluoromethylacrylic acid, and the like.

Examples of the derivative of the (meth)acrylic acid compound include halides of the (meth)acrylic acid compound, anhydrides of the (meth)acrylic acid compound, and the like.

Examples of the halides of the (meth)acrylic acid compound include acryloyl fluoride, acryloyl chloride, acryloyl bromide, acryloyl iodide, methacryloyl fluoride, methacryloyl chloride, methacryloyl bromide, methacryloyl iodide, 2-fluoroacryloyl fluoride, 2-fluoroacryloyl chloride, 2-fluoroacryloyl bromide, 2-fluoroacryloyl iodide, 2-trifluoromethylacryloyl fluoride, 2-trifluoromethylacryloyl chloride, 2-trifluoromethylacryloyl bromide, 2-trifluoromethylacryloyl iodide, and the like.

Examples of the anhydrides of the (meth)acrylic acid compound include acrylic anhydride, methacrylic anhydride, 2-fluoroacrylic anhydride, 2-trifluoromethylacrylic anhydride, and the like.

Examples of the basic catalyst include inorganic bases and organic amines such as sodium hydride, sodium hydroxide, potassium hydroxide, sodium carbonate, potassium carbonate, sodium hydrogen carbonate, potassium hydrogen carbonate, silver oxide, sodium phosphate, potassium phosphate, disodium monohydrogen phosphate, dipotassium monohydrogen phosphate, monosodium dihydrogen phosphate, monopotassium dihydrogen phosphate, sodium methoxide, potassium t-butoxide, triethylamine, tributylamine, trioctylamine, pyridine, N,N-dimethylaminopyridine, 1,5-diazabicyclo[4,3,0]non-5-ene (DBN), and 1,8-diazabicyclo[5,4,0]undec-7-ene (DBU). These basic catalysts may be used either alone or in combination.

Esterification may be implemented by reacting a base (catalyst) with the homoadamantane derivative represented by the formula (A) and the (meth)acrylic acid compound or its derivative. Esterification may be implemented in the presence or absence of an organic solvent. When using an organic solvent, it is preferable to adjust the substrate concentration within a range of about 0.1 to about 10 mol/L. When the substrate concentration is 0.1 mol/L or more, the desired amount of product can be obtained using a normal reactor (i.e., it is economical). When the substrate concentration is 10 mol/L or less, the temperature of the reaction mixture can be easily controlled.

Specific examples of the solvent used for the above reaction include saturated hydrocarbons such as octane, nonane, decane, undecane, cyclohexane, methylcyclohexane, and ethylcyclohexane, aromatic hydrocarbons such as toluene, xylene, and mesitylene, oxygen-containing hydrocarbons such as cyclohexanone, dipropyl ether, dibutyl ether, and tetrahydrofuran, halogen-containing hydrocarbons such as dibromomethane, carbon tetrachloride, and 1,2-dichloroethane, and the like.

The reaction temperature is about −200 to about 200° C., and preferably 0 to 100° C. When using the basic catalyst, it is particularly preferable to adjust the reaction temperature within a range of 0 to 50° C. so that polymerization does not occur. The reaction temperature is still more preferably 0 to 30° C. The reaction pressure (absolute pressure) is about 0.01 to about 10 MPa, and preferably normal pressure to 1 MPa, for example.

The homoadamantane derivative represented by the formula (I) may also be produced by reacting the homoadamantane derivative represented by the formula (A) with the (meth)acrylic acid compound or its derivative in the presence of an acid catalyst. An acid having a Hammett acidity function $H_0$ of −10.3 or less is preferably used as the acid catalyst. Specific values of the acidity function are described in "*Kagaku Binran Kisohen II* (Handbook of Chemistry)", 4th edition, The Chemical Society of Japan (editor), pp. 323-324, for example. Specific examples of the acid that may be used for the above reaction include $CF_3SO_3H$, $C_2F_5SO_3H$, $C_3F_7SO_3H$, $C_4F_9SO_3H$, $C_5F_{11}SO_3H$, $C_6F_{13}SO_3H$, $H_2S_2O_7$, $HClO_4$, $ClSO_3H$, $FSO_3H$, and the like.

When using the acid catalyst, the reaction temperature is about −200 to about 200° C., and preferably 70 to 1400° C. When using the acid catalyst, the reaction rate may decrease when the boiling point is less than 70° C., since the dehydration efficiency due to azeotropy with water is low. When the boiling point is more than 200° C., (meth)acrylic acid may be polymerized due to a high reaction temperature, so that the yield may decrease. The reaction pressure (absolute pressure) is about 0.01 to about 10 MPa, and preferably normal pressure to 1 MPa, for example. When an aromatic hydrocarbon solvent such as benzene or toluene is used, a Friedel-Crafts reaction product may be produced due to a reaction between the compound represented by the formula (I) or the (meth)acrylic acid compound or its derivative, and a carbocation produced due to the acid catalyst.

Specific examples of the solvent used for the above reaction include saturated hydrocarbons such as octane, nonane, decane, undecane, cyclohexane, methylcyclohexane, and ethylcyclohexane, aromatic hydrocarbons such as toluene, xylene, and mesitylene, oxygen-containing hydrocarbons such as cyclohexanone, dipropyl ether, dibutyl ether, and tetrahydrofuran, halogen-containing hydrocarbons such as dibromomethane, carbon tetrachloride, and 1,2-dichloroethane, and the like.

It is preferable to use a hydrocarbon solvent such as cyclohexane, ethylcyclohexane, toluene, or xylene when utilizing an azeotropic dehydration reaction. The molar ratio of the reaction reagent (acid catalyst) to the compound represented by the formula (A) (i.e., alicyclic structure-containing alcohol) is about 0.01 to about 100, and preferably 1 to 1.5, for example.

After completion of the reaction, the reaction mixture is separated into an aqueous layer and an organic layer, and the product is optionally extracted from the aqueous layer. The target compound represented by the formula (I) is obtained by evaporating the solvent from the reaction mixture under reduced pressure. The reaction mixture may optionally be purified, or may be used directly for the subsequent reaction without purification. The purification method may be selected from distillation, extraction/washing, crystallization, activated carbon absorption, silica gel column chromatography, and the like taking account of the production scale and the desired purity. It is preferable to use extraction/washing or crystallization since the handling operation can be performed at a relatively low temperature, and a large amount of sample can be treated at one time.

A (meth)acrylic polymer according to the invention is obtained by polymerizing the compound represented by the formula (I).

The (meth)acrylic polymer includes repeating units derived from one or more types of the compound represented by the formula (I). The (meth)acrylic polymer may be a homopolymer obtained by polymerizing only one type of the compound represented by the formula (I), or may be a coopolymer obtained by polymerizing two or more types of the compound represented by the formula (I), or may be a coopolymer obtained by polymerizing one or more types of the compound represented by the formula (I) and an additional polymerizable monomer.

It is preferable that the content of the repeating unit derived from the compound represented by the formula (I) in the (meth)acrylic polymer be 10 to 90 mol %, and more preferably 25 to 75 mol %.

The weight average molecular weight (Mw) of the (meth)acrylic polymer is preferably 1000 to 100,000, and more preferably 2000 to 10,000. If the weight average molecular weight of the (meth)acrylic polymer is too low, the resulting resin may not maintain its shape. If the weight average molecular weight of the (meth)acrylic polymer is too high, it may be impossible to develop the resulting resist.

The dispersity (Mw/Mn) of the (meth)acrylic polymer is preferably 1 to 3, and more preferably 1 to 2. If the dispersity of the (meth)acrylic polymer is too large, the composition of the resulting resist may be non-uniform. Therefore, it is most preferable that the (meth)acrylic polymer have a dispersity of 1 (monodisperse).

The polymerization method is not particularly limited. For example, a known polymerization method such as solution polymerization (polymerization at the boiling point, or polymerization at a temperature less than the boiling point), emulsion polymerization, suspension polymerization, or bulk polymerization may be used. It is preferable that the amount of unreacted high-boiling monomer that remains in the reaction mixture after polymerization be as small as possible. It is preferable to optionally remove unreacted monomer during or after polymerization.

It is preferable to implement the polymerization reaction in a solvent using a radical initiator. Examples of the initiator include, but are not limited to, peroxide initiators, azo initiators, and the like.

Examples of the peroxide initiators include organic peroxides such as peroxycarbonates, ketone peroxides, peroxyketals, hydroperoxides, dialkyl peroxides, diacyl peroxides, and peroxyesters (e.g., lauroyl peroxide and benzoyl peroxide). Examples of the azo initiators include azo compounds such as 2,2'-azobisisobutyronitrile, 2,2'-azobis(2-methylbutyronitrile), 2,2'-azobis(2,4-dimethylvaleronitrile), and dimethyl 2,2'-azobis(isobutyrate), and the like.

These initiators may be appropriately used either alone or in combination depending on the reaction conditions (e.g., polymerization temperature).

After completion of polymerization, the compound represented by the formula (I) or an additional copolymerizable monomer may be removed from the resulting polymer using various methods. It is preferable to wash the (meth)acrylic polymer using a poor solvent for the (meth)acrylic polymer from the viewpoint of operability and cost. It is preferable that the poor solvent have a low boiling point. Examples of such a poor solvent include methanol, ethanol, n-hexane, n-heptane, and the like.

The (meth)acrylic polymer according to the invention may be used for a positive photoresist. Specifically, the homoadamantane skeleton of the highly reactive homoadamantane derivative represented by the formula (I) can be introduced into a PAG, a low-molecular-weight positive photoresist, a positive photoresist monomer, or a positive photoresist polymer.

Since an adamantane skeleton and a lactone skeleton are introduced into the (meth)acrylic polymer according to the invention using a monomer that includes an adamantane skeleton and a lactone skeleton instead of separately using a monomer that includes an adamantane skeleton and a monomer that includes a lactone skeleton, the adamantane skeleton and the lactone skeleton are more uniformly dispersed in the (meth)acrylic polymer (photoresist resin), so that a reduction in roughness can be achieved.

A resin composition that includes the (meth)acrylic polymer according to the invention may be used for various applications such as a circuit-forming material (e.g., semiconductor production resist and printed circuit board) and an image-forming material (e.g., printing plate material and relief image). It is preferable to use the resin composition as a photoresist resin composition, and it is more preferable to use the resin composition as a positive photoresist resin composition.

A positive photoresist composition according to the invention includes the (meth)acrylic polymer according to the invention, and a photoacid generator. It is preferable that the positive photoresist composition include the (meth) acrylic polymer in an amount of 2 to 50 parts by mass, and more preferably 5 to 15 parts by mass, based on 100 parts by mass of the positive photoresist composition.

The positive photoresist composition may include a quencher (e.g., organic amine), an akali-soluble component such as an alkali-soluble resin (e.g., novolac resin, phenol resin, imide resin, and carboxyl group-containing resin), a coloring agent (e.g., dye), an organic solvent (e.g., hydrocarbon, halogenated hydrocarbon, alcohol, ester, ketone, ether, cellosolve, carbitol, glycol ether ester, and mixture thereof), and the like in addition to the (meth)acrylic polymer and the PAG (photoacid generator).

A compound that efficiently generates an acid upon exposure may be used as the photoacid generator. Examples of the photoacid generator include diazonium salts, iodonium salts (e.g., diphenyliodonium hexafluorophosphate), sulfonium salts (e.g., triphenylsulfonium hexafluoroantimonate, triphenylsulfonium hexafluorophosphate, and triphenylsulfonium methanesulfonate), sulfonates (e.g., 1-phenyl-1-(4-methylphenyl)sulfonyloxy-1-benzoylmethane, 1,2,3-trisulfonyloxymethylbenzene, 1,3-dinitro-2-(4-phenylsulfonyloxymethyl)benzene, 1-phenyl-1-(4-methylphenylsulfonyloxymethyl)-1-hydroxy-1-benzoylmethane), oxathiazole derivatives, s-triazine derivatives, disulfone derivatives (e.g., diphenyl disulfone), imide compounds, oxime sulfonate, diazonaphthoquinone, benzoin tosylate, and the like. These photoacid generators may be used either alone or in combination.

The content of the photoacid generator in the positive photoresist composition may be appropriately selected depending on the acidity of an acid generated upon exposure (irradiation), the content of the structural unit derived from the compound represented by the formula (I) in the (meth) acrylic polymer, and the like.

The photoacid generator is preferably used in an amount of 0.1 to 30 parts by mass, more preferably 1 to 25 parts by mass, and still more preferably 2 to 20 parts by mass, based on 100 parts by mass of the (meth)acrylic polymer.

The positive photoresist composition may be prepared by mixing the (meth)acrylic polymer and the photoacid generator optionally together with the organic solvent and the like, and optionally removing impurities using a known solid separation means (e.g., filter).

A fine pattern can be formed with high accuracy by applying the positive photoresist composition to a base material or a substrate, drying the positive photoresist composition to form a film, exposing the film (resist film) through a given mask (and optionally baking the film) to form a latent pattern, and developing the film.

The invention also provides a method for forming a resist pattern that includes the steps of forming a resist film on a substrate using the positive photoresist composition, selectively exposing the resist film to light, and subjecting the resist film which has been selectively exposed to an alkaline development treatment to form a resist pattern.

Examples of the substrate include a silicon wafer, a metal, a plastic, glass, a ceramic, and the like. The resist film may be formed using the positive photoresist composition by utilizing a known coating means such as a spin coater, a dip coater, or a roller coater. The thickness of the resist film is preferably 50 nm to 20 μm, and more preferably 100 nm to 2 μm.

The resist film may be selectively exposed using light having an arbitrary wavelength (e.g., ultraviolet rays or X-rays). A semiconductor resist is normally exposed using a g-line, an i-line, excimer laser light (e.g., XeCl, KrF, KrCl, ArF, or ArCl), soft X-rays, or the like. The exposure dose (energy) is about 0.1 to about 1000 mJ/cm$^2$, and preferably about 1 to about 100 mJ/cm$^2$, for example.

The (meth)acrylic polymer included in the positive resist composition according to the invention has acid-labile properties. When an acid is generated from the photoacid generator upon selection exposure, the cyclic part of the structural unit derived from the compound represented by the formula (I) that is included in the (meth)acrylic polymer promptly dissociates due to the acid to produce a carboxyl group or a hydroxyl group that contributes to solubilization. Therefore, a given pattern can be formed with high accuracy by developing the resist film using an alkaline developer.

EXAMPLES

The invention is further described below by way of examples and comparative examples. Note that the invention is not limited to the following examples.

The properties were measured by the following methods.
(1) Nuclear magnetic resonance spectroscopy (NMR): Chloroform-d was used as a solvent, and a spectrometer "JNM-ECA500" (manufactured by JEOL Ltd.) was used as a measurement system.
(2) Gas chromatograph-mass spectrometry (GC-MS): A spectrometer "GCMS-QP2010" (manufactured by Shimadzu Corporation, EI mode) was used as a measurement system.
(3) Weight average molecular weight (Mw) and dispersity (Mw/Mn): The weight average molecular weight (Mw) and the dispersity (Mw/Mn) were measured as a polystyrene-reduced value using an HLC-8220 GPC system (manufactured by Tosoh Corporation, column: TSGgel G-4000HXL+ G-2000HXL).

Production Example 1

Synthesis of 4-methanesulfonyloxy-2-adamantanone 599.62 g (3.6 mol) of 4-hydroxy-2-adamantanone and 655 mL (4.7 mol) of triethylamine were dissolved in 2.5 L of tetrahydrofuran (THF). 310 mL (4.0 mol) of methanesulfonic chloride was slowly added dropwise to the solution. After the addition of methanesulfonic chloride over about 1.5 hours while appropriately removing heat, the mixture was reacted for 2 hours. After the addition of 1 L of water to the reaction mixture, the mixture was treated by a normal method to obtain 785.74 g of 4-methanesulfonyloxy-2-adamantanone represented by the following formula (3.2 mol, yield: 89.2%, GC purity: 99.9%). Note that Ms in the formula is a methanesulfonyl group.

GC-MS: 244 (M$^+$, 11.3%), 165 (15.3%), 148 (27.4%), 120 (43.7%), 91 (29.2%), 79 (100%)

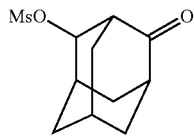

Production Example 2

Synthesis 1 of
endo-bicyclo[3.3.1]-6-nonene-3-carboxylic acid

A mixture of 250.52 g (1.0 mol) of 4-methanesulfonyloxy-2-adamantanone synthesized in Production Example 1, 460 mL of ethanol, 500 mL (9.5 mol) of a 50% sodium hydroxide aqueous solution, and 1.2 L of water was reacted at a reflux temperature for 2 hours, and cooled to room temperature. After removing organic impurities contained in the reaction solution by extraction, the reaction solution was made acidic using concentrated hydrochloric acid to precipitate a white solid. The white solid was filtered off, and the resulting white cake was dissolved in 1.5 L of THF. After performing an oil/water separation operation, the mixture was treated by a normal method to obtain 501.52 g of endo-bicyclo[3.3.1]-6-nonene-3-carboxylic acid represented by the following formula (3.0 mol, yield: 76.4%, GC purity: 99.2%).

GC-MS: 166 (M$^+$, 4.7%), 148 (25.4%), 120 (15.5%), 91 (18.9%), 79 (100%)

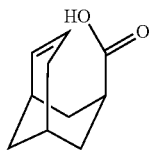 [SMILES: O=C(O)C1CC2C=CCC(C2)C1]

Production Example 3

Synthesis 2 of
endo-bicyclo[3.3.1]-6-nonene-3-carboxylic acid 2.9 g (45 mmol) of sodium azide was added to a slurry of 4.5 g (30 mmol) of 2-adamantanone and 15 mL (231 mmol) of methanesulfonic acid at room temperature over about 30 minutes (i.e., separately added more than a dozen times). The mixture was reacted at 50° C. for 1 hour. After the addition of 34 mL of ethanol, 36 mL (682 mmol) of a 50 wt % sodium hydroxide aqueous solution, and 79 mL of water to the mixture, the mixture was reacted at a reflux temperature for 2 hours, and cooled to room temperature. The subsequent operation was performed in the same manner as in Production Example 2 to obtain 3.6 g of endo-bicyclo[3.3.1]-6-nonene-3-carboxylic acid represented by the following formula (21 mmol, yield: 71.4%, GC purity: 96.8%).

Production Example 4

Synthesis of 4-oxa-5-oxo-5-homo-2-adamantanol 52 mL (509 mmol) of a 30 wt % hydrogen peroxide solution was slowly added dropwise to a slurry of 45.0 g (271 mmol) of endo-bicyclo[3.3.1]-6-nonene-3-carboxylic acid synthesized in Production Example 2 or 3 and 38 mL (1.0 mol) of formic acid. The mixture was maintained at 45° C. or less during the addition of the 30 wt % hydrogen peroxide solution while removing heat using a water bath. After the addition, the mixture was reacted for 3 hours. Sodium hydrogen sulfite was added to the reaction mixture until foaming did not occur, and excess hydrogen peroxide was quenched. The mixture was then neutralized to a pH of about 8 using sodium hydroxide and sodium hydrogen carbonate. The mixture was then treated by a normal method to obtain 43.7 g of 4-oxa-5-oxo-5-homo-2-adamantanol represented by the following formula (240 mmol, yield: 88.5%, GC purity: 96.8%). 4-Oxa-5-oxo-5-homo-2-adamantanol obtained by the method of Production Examples 1 to 4 has high purity and a low isomer content as compared with a product obtained by directly oxidizing 4-hydroxy-2-adamantanone.

GC-MS: 182 (M$^+$, 7.4%), 154 (20.7%), 136 (11.5%), 120 (15.9%), 110 (32.4%), 95 (43.1%), 79 (100%), 66 (76.4%), 57 (43.4%), 41 (40.5%)

$^1$H-NMR: 1.46 (dd, J=2.9 Hz, 13.2 Hz, 1H), 1.82-1.98 (m, 5H), 2.07 (d, J=13.2 Hz, 2H), 2.17 (d, J=13.2 Hz, 1H), 2.34 (ddt, J=1.1 Hz, 4.6 Hz, 15.7 Hz, 1H), 3.02-3.04 (m, 1H), 3.46 (br-s, 1H), 3.94 (s, 1H), 4.27 (dd, J=2.0 Hz, 2.3 Hz, 1H)

$^{13}$C-NMR: 25.37, 27.25, 29.30, 30.56, 30.94, 32.32, 40.68, 70.49, 76.09, 178.76

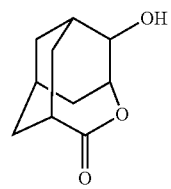 [SMILES: O=C1OC2CC3CC1CC(C3)C2O]

Example 1

Synthesis of 4-oxa-5-oxo-5-homo-2-adamantyl methacrylate 40.0 g (200 mmol) of 4-oxa-5-oxo-5-homo-2-adamantanol synthesized in Production Example 4, 46 mL (330 mmol) of triethylamine, 2.7 g (22 mmol) of 4-dimethylaminopyridine, and 40 mg (0.1 wt %) of p-methoxyphenol were dissolved in 200 mL of THF. The solution was stirred for about 1 hour while bubbling dry air into the solution. 39 mL (264 mmol) of methacrylic anhydride was added dropwise to the solution over about 1 hour. Heat was optionally removed using a water bath during the above operation. After stirring the mixture for 3 hours, the mixture was treated by a normal method to obtain 4-oxa-5-oxo-5-homo- 2-adamantyl methacrylate represented by the following formula (49.2 g, yield: 89.3%, GC purity: 97.1%, GPC purity: 97.4%).

GC-MS: 250 (M+, 0.1%), 232 (0.6%), 204 (1.1%), 181 (0.7%), 164 (38.6%), 136 (40.5%), 121 (8.0%), 108 (7.3%), 92 (21.1%), 79 (39.0%), 69 (100%), 55 (10.3%), 41 (61.8%)

$^1$H-NMR: 1.59 (d, J=12.8 Hz, 1H), 1.91-2.22 (m, 8H), 1.97 (s, 3H), 2.26 (dt, J=15.3 Hz, 4.8 Hz, 1H), 3.10 (br-s, 1H), 4.31 (d, J=2.1 Hz, 1H), 5.06 (s, 1H), 5.64 (t, J=1.3 Hz, 1H), 6.15 (s, 1H)

$^{13}$C-NMR: 17.85, 24.83, 27.87, 28.53, 29.64, 30.21, 31.65, 40.27, 71.74, 72.34, 125.86, 135.66, 165.20, 176.76

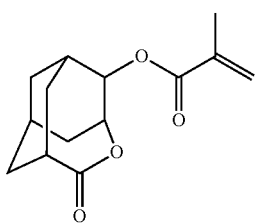 [SMILES: C=C(C)C(=O)OC1C2CC3CC(C2)C(=O)OC1C3]

Comparative Example 1

Synthesis of 4-oxa-5-oxo-5-homo-1-adamantyl methacrylate 4-oxa-5-oxo-5-homo-1-adamantyl methacrylate represented by the following formula was obtained in the same manner as in Example 1, except that 4-oxa-5-oxo-5-homo-1-adamantanol was used instead of 4-oxa-5-oxo-5-homo-2-adamantanol. The raw material conversion rate after 10 hours was 50.6%, and the selectivity of 4-oxa-5-oxo-5-homo-1-adamantyl methacrylate was 51.4%.

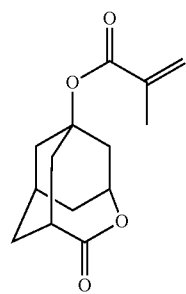 [SMILES: C=C(C)C(=O)OC12CC3CC(C1)OC(=O)C(C3)C2]

Evaluation Example 1

Comparison of Dipole Moment of Compounds Synthesized in Example 1 and Comparative Example 1

A dipole change when rotating the carbon-oxygen bond axis that connects the homoadamantane skeleton and the ester moiety by 360° (see the arrow in the following formula) was compared between the compound synthesized in Example 1 (compound A) and the compound synthesized in Comparative Example 1 (compound B).

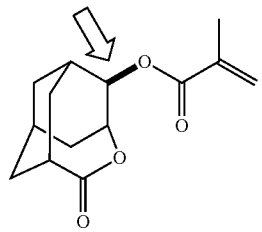

Compound A

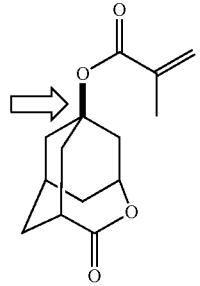

Compound B

FIG. 1 illustrates the dipole moment calculation results using molecular orbital calculations (MOPAC PM5). As illustrated in FIG. 1, the compound synthesized in Example 1 (compound A) had a dipole moment higher than that of the compound synthesized in Comparative Example 1 (compound B) by up to 1 debye. It was thus confirmed the compound synthesized in Example 1 (compound A) had high polarity as compared with the compound synthesized in Comparative Example 1 (compound B). It is expected that the compound synthesized in Example 1 (compound A) exhibits high solubility in various polymerization solvents, coating solvents, resist developers, and the like.

Example 2

Synthesis of (meth)acrylic copolymer

Dimethyl 2,2'-azobis(isobutyrate), a monomer A, a monomer B, and a monomer C (compound synthesized in Example 1) were added to methyl isobutyl ketone in a ratio of 0.1/2.0/1.0/1.0, and the mixture was stirred for 6 hours under reflux with heating. An operation of pouring the reaction mixture into a mixed solvent of a large quantity of methanol and water to effect precipitation was performed three times to effect purification to obtain a copolymer. The compositional ratio (A:B:C) (mol) of the copolymer was 29:30:41. The copolymer had a weight average molecular weight (Mw) of 7018 and a dispersity (Mw/Mn) of 1.83.

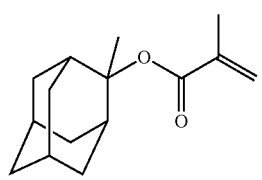

Monomer A

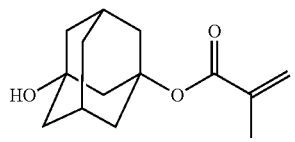

Monomer B

Example 3

Preparation of Positive Resist Composition 5 parts by mass of triphenylsulfonium nonafluorobutanesulfonate (photoacid generator) was added to 100 parts by mass of the copolymer obtained in Example 2. 10 parts by mass of the mixture was dissolved in 90 parts by mass of propylene glycol monomethyl ether acetate to prepare a resist composition. The resist composition was applied to a silicon wafer, and baked at 110° C. for 60 seconds to form a resist film. The wafer was subjected to open exposure at a dose of 100 mJ/cm² using 248 nm light. The resist film was baked at 110° C. for 60 seconds immediately after exposure, and developed for 60 seconds using a tetramethylammonium hydroxide aqueous solution (2.38 mass %). The resist film was completely removed by development.

It was thus confirmed that a composition that includes the (meth)acrylic polymer according to the invention functions as a positive photoresist composition.

INDUSTRIAL APPLICABILITY

A resin composition that includes the (meth)acrylic polymer according to the invention may be used as a circuit-forming material (e.g., semiconductor production resist and printed circuit board), an image-forming material (e.g., printing plate material and relief image), and the like. The resin composition may suitably be used as a positive photoresist resin composition.

Although only some exemplary embodiments and/or examples of the invention have been described in detail above, those skilled in the art will readily appreciate that many modifications are possible in the exemplary embodiments and/or examples without materially departing from the novel teachings and advantages of the invention. Accordingly, all such modifications are intended to be included within the scope of the invention.

The documents described in the specification are incorporated herein by reference in their entirety.

The invention claimed is:

1. A compound represented by the following formula

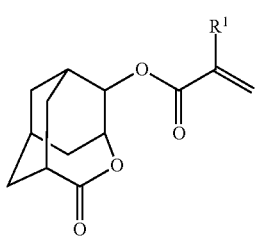

(I)

wherein R¹ is a hydrogen atom or a methyl group.

2. A method for producing the compound according to claim 1, comprising reacting 5-oxo-4-oxa-5-homoadamantan-2-ol represented by the following formula (A) with a (meth)acrylic acid compound or its derivative.

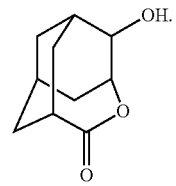

(A)

3. The production method according to claim 1, wherein the 5-oxo-4-oxa-5-homoadamantan-2-ol is reacted with methacrylic anhydride.

4. A (meth)acrylic polymer obtained by polymerizing one or more compounds of formula (I) according to claim 1.

5. A positive photoresist composition comprising the (meth)acrylic polymer according to claim 4 and a photoacid generator.

6. A method for forming a resist pattern comprising:
   forming a photoresist film on a substrate comprising the positive photoresist composition according to claim 5;
   selectively exposing the photoresist film to light; and
   subjecting the photoresist film which has been selectively exposed to light to an alkaline development treatment to form a resist pattern.

7. The (meth)acrylic polymer according to claim 4, which is a homopolymer.

8. The (meth)acrylic polymer according to claim 4, which is a copolymer.

9. The (meth)acrylic polymer according to claim 4, obtained by polymerizing said one or more compounds of formula (I) and at least one additional polymerizable monomer.

10. The (meth)acrylic polymer according to claim 9, obtained by polymerizing said one or more compounds of formula (I) and two additional polymerizable monomers.

11. The (meth)acrylic polymer according to claim 10, wherein the two additional polymerizable monomers are Monomer A and Monomer B having the following structures:

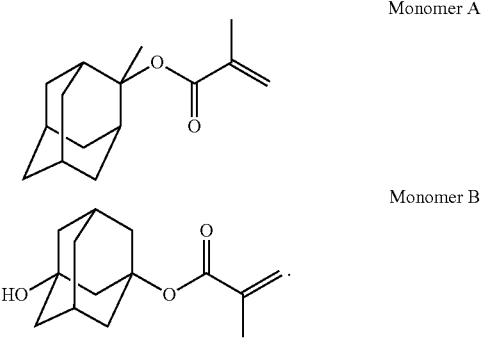

12. The compound according to claim 1, wherein R¹ is a hydrogen atom.

13. The compound according to claim 1, wherein R¹ is a methyl group.

14. The (meth)acrylic polymer according to claim 11, wherein a content of a repeating unit derived from the compound represented by formula (I) in the (meth)acrylic polymer is 25 to 75 mol %.

* * * * *

UNITED STATES PATENT AND TRADEMARK OFFICE
CERTIFICATE OF CORRECTION

PATENT NO. : 9,513,545 B2
APPLICATION NO. : 13/816071
DATED : December 6, 2016
INVENTOR(S) : Shinji Tanaka et al.

It is certified that error appears in the above-identified patent and that said Letters Patent is hereby corrected as shown below:

In the Claims

Column 14, Line 11, "3. The production method according to claim 1, wherein" should read -- 3. The production method according to claim 2, wherein --

Signed and Sealed this
Twenty-third Day of May, 2017

Michelle K. Lee
*Director of the United States Patent and Trademark Office*